United States Patent [19]

Hoffman

[11] 4,209,859
[45] Jul. 1, 1980

[54] LIGAMENT AND TENDON PROSTHESIS OF POLYETHYLENE TEREPHTHALATE AND METHOD OF PREPARING SAME

[75] Inventor: Harmon L. Hoffman, Wyckoff, N.J.

[73] Assignee: Meadox Medicals, Inc., Oakland, N.J.

[21] Appl. No.: 891,433

[22] Filed: Mar. 29, 1978

[51] Int. Cl.² .......................... A61F 1/24; A61F 1/00
[52] U.S. Cl. .................................. 3/1; 3/1.4; 3/1.9; 128/334 R
[58] Field of Search .............. 3/1, 1.4, 1.9, 1.91; 128/334 R

[56] References Cited

U.S. PATENT DOCUMENTS

| | | | |
|---|---|---|---|
| 2,990,605 | 7/1961 | Demsyk | 3/1.4 X |
| 3,513,484 | 5/1970 | Hausner | 3/1 |
| 3,613,120 | 10/1971 | McFarland, Jr. | 3/1.91 |
| 3,797,047 | 3/1974 | Pillet | 3/1 |
| 3,805,300 | 4/1974 | Tascon-Alonso et al. | 3/1 |
| 4,047,252 | 9/1977 | Liebig et al. | 3/1.4 |
| 4,127,902 | 12/1978 | Homsy | 3/1 |

*Primary Examiner*—Ronald L. Frinks
*Attorney, Agent, or Firm*—Blum, Kaplan, Friedman, Silberman & Beran

[57] ABSTRACT

Prosthesis suitable for replacing or supplementing damaged ligaments or tendons are prepared from polyethylene terephthalate strips by treating such strips with a shrinking agent under restraint in the longitudinal direction. The treatment reduces substantially the extensibility of the fabric in the longitudinal direction. Stiffness can be imparted to the strips by forming the strips into tubes which may have longitudinally-extending ridges thereon and heat-setting same.

17 Claims, 5 Drawing Figures

ELONGATION OF DACRON PROSTHESES UNDER STRESS

LIGAMENT AND TENDON PROSTHESIS OF POLYETHYLENE TEREPHTHALATE AND METHOD OF PREPARING SAME

BACKGROUND OF THE INVENTION

The need for splints or artificial ligaments to replace or supplement natural ligaments and tendons where such ligaments and tendons have suffered damage, usually accidental, is sufficiently widespread so that conferences have been held on the subject and the problem has been discussed in reports by orthopedic surgeons. An example of a frequently-occurring injury requiring a device of this kind for satisfactory surgical repair is an acromioclavicular dislocation, in which the injury is produced by falling on the point of the shoulder with the arm in the adducted position. By this action one or more of the ligaments confining the acromioclavicular joint may become ruptured, and surfical repair utilizing an appropriate splinting device, to provide internal support for the damaged ligaments, is frequently indicated. Other ligaments such as the medial collateral and anterior cruciate may be similarly repaired.

These constructions may also be useful in surgical reconstruction of damaged tendons including achilles and patellar tendons, and possibly flexor digital tendons. Tendons possess a very poor capacity for self-regeneration, and thus require very long periods of time to effect their own repair without the assistance of a prosthetic implant.

Surgeons who are experienced in the repair of ligament and tendon damage have recommended several desirable characteristics for materials (or constructions) to be applied as internal splints:

(1) The material must be capable of exerting mechanical strength equal to that of the damaged ligament, at least under moderate stress activity.

(2) It must have sufficient resistance to elongation under stress that it will retain its mechanical effectiveness.

(3) The material should be acceptable for permanent implant in the human body, preferably without the necessity for removal by a second operation. An important condition for good acceptability is that the material be sufficiently porous so as to permit invasion by the host tissues.

(4) The splint should permit early activity.

Primarily on account of their desirable characteristics of strength, porosity, and flexibility, the attention of surgeons was directed to woven and knitted Dacron (polyethylene terephthalate, Du Pont) tubular constructions used in vascular surgery as potential materials of construction for ligament splints. However, it has been found that Dacron prosthesis in the constructions conventionally used have inadequate resistance to elongation under stress, the elongation reaching values as high as 150%. Further, it is highly desirable that the cross-section of the prosthesis be such that it will be invaded by the host tissue and that an encasement be provided for formation of a living structure which will supplement the prosthesis.

As is evident, then, a structure which provides for greater resistance to elongation and which is sufficiently rigid so that a tubular structure with an open lumen can be provided is highly to be desired.

SUMMARY OF THE INVENTION

To prepare a prosthesis in accordance with the present invention, a fabric strip is restrained from shrinking in the lengthwise direction and is then treated with a shrinking agent under conditions such that the extensibility of the fabric strip is reduced by at least about 50%. The strip may be flat or in tubular form, generally, in flattened tubular form.

To provide rigidity, the strip may be formed into a tubular form, slipped onto a mandrel and then heat-set, as by treatment at about 250° F. for about 3 minutes. In addition to providing rigidity, the heat-setting operation provides an open lumen for invasion by host tissue.

In a preferred form, at least one surface of the strip is of velour construction, the velour surface facilitating adhesion of host tissue thereto. Also, the fabric may be of woven, circularly-knit or warp-knit construction.

Accordingly, an object of the present invention is a method of preparing a Dacron prosthesis of reduced extensibility suitable for implantation in a patient for replacement or supplementation or repair of a damaged ligament or tendon.

Another object of the present invention is a method of preparing a prosthesis of increased rigidity and having an open lumen for repair, supplementation or replacement of a damaged ligament or tendon in a patient.

A further object of the present invention is a method of treatment of a patient suffering from a damaged ligament or tendon, said treatment comprising the use of a prosthesis of Dacron having improved properties, specifically with respect to extensibility and facilitation of ingrowth of host tissue.

Still another object of the present invention is a prosthesis suitable for repair, supplementation or replacement of a damaged ligament or tendon.

An important object of the present invention is a prosthesis suitable for repair, supplementation or replacement of a damaged ligament or tendon in a patient, where the prosthesis has reduced extensibility and enhanced properties with respect to ingrowth of host tissue.

Still other objects and advantages of the invention will in part be obvious and will in part be apparent from the specification.

The invention accordingly comprises the several steps and the relation of one or more of such steps with respect to each of the others in the methods taught, and the article possessing the features, properties, and the relation of elements, which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREDERRED EMBODIMENTS

The Dacron fabric to be used in the process of the present invention may be initially in the form of a flat strip or may be a flattened tube prepared by weaving, circular-knitting or warp-knitting. Where the material is a flat strip, it may be woven or warp-knit. Where the material is clean, as received, it may be subjected to a shrinking or compacting treatment as received. Otherwise, the material is cleaned by conventional washing or scouring to remove sizing, oils, or any other foreign matter.

Figure 5:
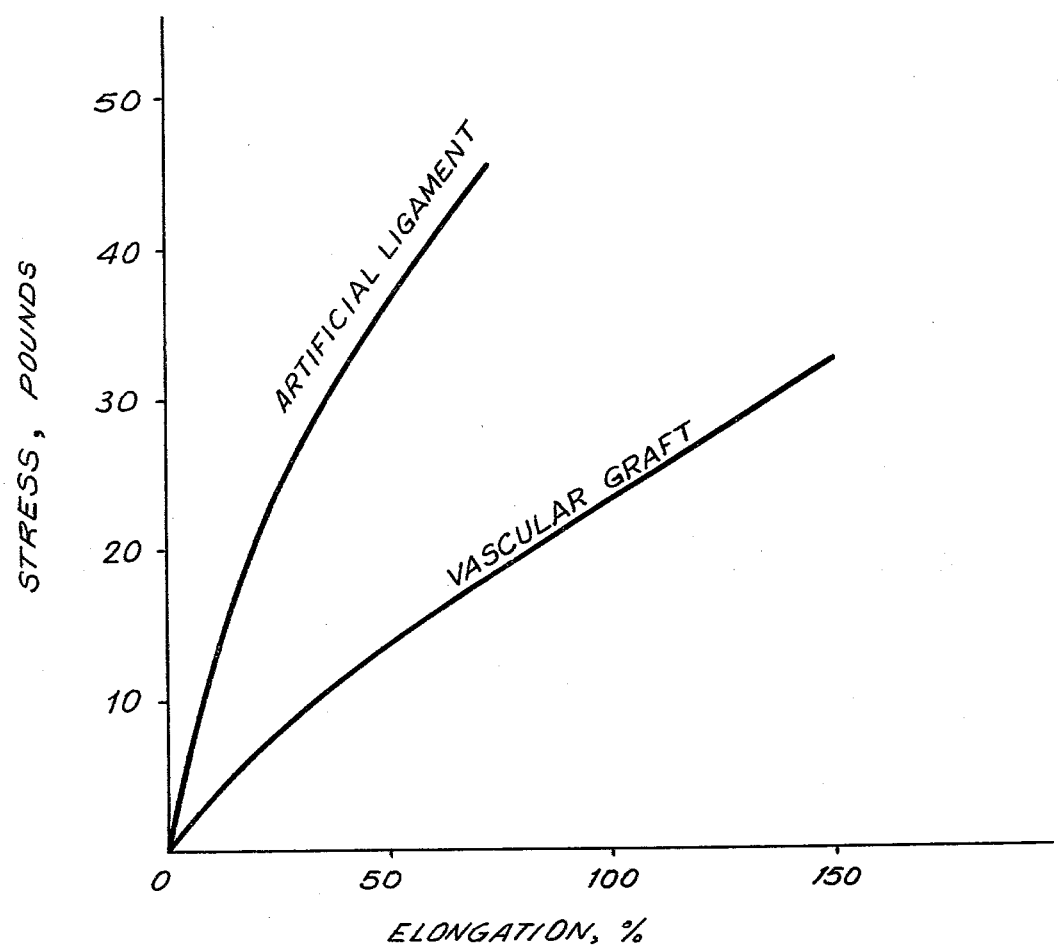
FIG. 5 is a graph showing the elongation under stress of an artificial ligament prepared in accordance with the present invention and a vascular graft prepared by conventional methods.

It is conventional to compact knitted Dacron products by a process currently in use, preferred shrinking agents being $CH_2Cl_2$ and $CH_2Cl_2$ in combination with $NO_2$. Conventionally, the material is simply exposed to the shrinking agent to effect the desired degree of compaction, the principal objective being to reduce the size of the openings between the threads constituting the fabric. However, such fabrics, subsequent to the shrinking operation, have a degree of extensibility as shown in the lower curve of FIG. 5 which is so great that a splint made from such a fabric fails to provide the required support. I have found that subjecting the fabric to compaction with the shrinking agent under restraint in the longitudinal direction greatly reduces the extensibility of the compacted fabric. In general, the elongation at a given stress should be reduced by at least 50%. Preferably, the elongation should be reduced by about 60%. Thus, under a stress which in a conventionally-shrunk fabric which would produce an elongation of 150%, the elongation of a fabric treated in accordance with the present invention is only about 60% as can be seen from the upper curve in FIG. 5.

Figure 1:
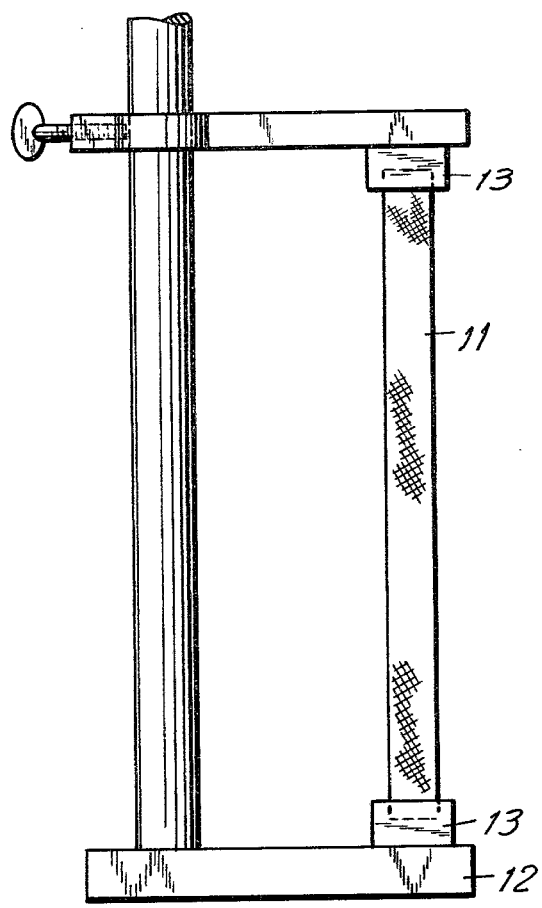
FIG. 1 shows a Dacron strip under restraint in preparation for treatment with a shrinking agent.

FIG. 1 shows schematically a fabric strip 11 held in a rigid framework 12 between clamps 13. The entire framework with the strip 11 held under restraint can be placed in a vessel, not shown, for treatment with the shrinking agent under the desired conditions of temperature and humidity.

Figure 2:
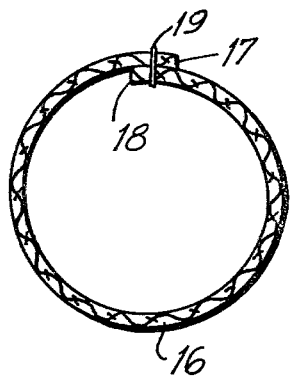
FIG. 2 is a sectional view of a Dacron strip formed into a tube.

The fabric strip can be either flat or tubular in construction during the compaction process step. However, I have found that it is desirable that the prosthesis to be implanted in a patient should be tubular, that is, should have an open lumen. The fabric strip, assuming that it is initially tubular in construction as when circularly-knit, woven or warp-knit in tubular form, and whether or not held in open tubular form during the compaction process, will collapse when removed from restraint. Accordingly, the strip is placed on a mandrel and is heat-set to provide the strip with some rigidity, the amount of rigidity provided being sufficient so that an open lumen will be maintained. FIG. 2 shows how a flat strip can be formed into a cylinder 16 by sewing the two edges 17 and 18 thereof together with Dacron thread 19. This tubular section can now be placed over a mandrel and heat-set in conventional fashion, as by heating for three minutes at 250° F.

Figure 3:
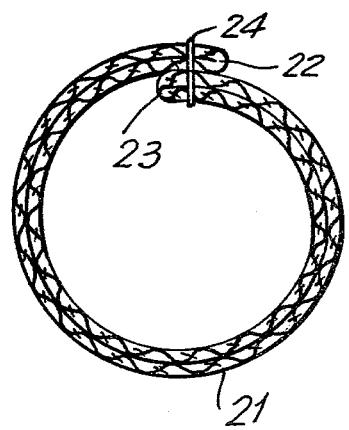
FIG. 3 is a sectional view of an initially-flattened tubular strip formed into a double-walled tube.

Another suitable construction is shown in FIG. 3, the strip in this case being a woven or knit tube in flattened form which is then formed into a double-walled cylinder 21 by sewing edges 22 and 23 together with Dacron thread 24. In this case, edges 22 and 23 are actually folds rather than true edges.

Figure 4:
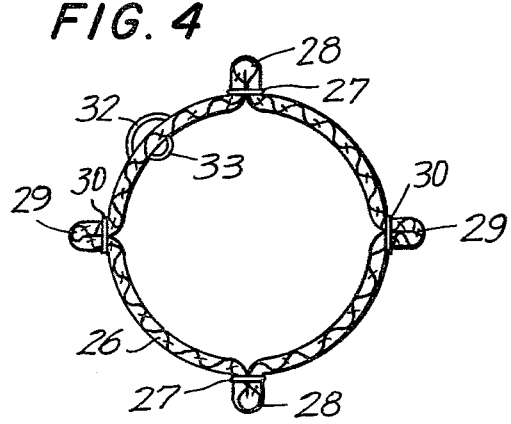
FIG. 4 is a sectional view of a Dacron tube in accordance with the present invention, said tube having longitudinally-extending ridges on the surface thereof.

The range of tendons to be supplemented or repaired or replaced is from about 2 mm in diameter to about 10 mm in diameter. For the smallest tendons, the construction of FIG. 2 is generally adequate so far as rigidity is concerned. For somewhat larger tendons say from about 3 mm to about 6 mm, the double-walled construction of FIG. 3 may give adequate rigidity. For the largest tendons, the construction shown in the prosthesis of FIG. 4 is preferred. This construction starts with a flattened tube having a circumference, or rather, periphery, in cross-section of between about 30 and about 70 mm. Starting with the flattened tube, the material being indicated by the reference numeral 26, the two layers comprising the flattened tube are sewn together longitudinally along lines about 2 mm in from each edge, using Dacron thread 27. The tube is then refolded so that each of the original ridges 28 lies between new folds 29. The new folds are similarly sewn together longitudinally using Dacron threads 30. The tubing, now having four ridges, is compacted by chemical treatment and is then heat-set on a mandrel as described above. Obviously the above procedure can be modified to provide any number of ridges from 1 upward to the point where the entire circumference of the tubing consists of ridges with virtually no tubing therebetween. However, from 3 to about 6 ridges are generally preferred, the larger number of ridges being used with larger tubing. Also, as can readily be seen, it is possible to start with the double-walled construction of FIG. 3 and then incorporate ridges thereon. Further, the height of the ridges is not limited to 2 mm, but this value has been found to be convenient for the sewing step and there is little increase in rigidity provided by corresponding increase in the height of the ridges.

The purpose of the open lumen in the constructions of FIGS. 2–4, as has already been noted, is to provide for ingrowth of body tissue. Such tissue must anchor to the Dacron strip as part of the process. The anchoring is facilitated if at least one surface is of the well-known velour structure. This structure is indicated in FIG. 4 by exterior loop 32 and interior loop 33. Tests have shown that the velour construction accelerates ingrowth of body tissue and provides firm anchorage for same. Clinical results have been obtained on twenty-five patients who sustained a Type III separation of the acromioclavicular joint. All of these patients were treated by the method of internal fixation. The patients ranged in age from 17 to 67 years, with an average of 33 years. The patients were followed for periods ranging from 12 months to six years, the average period of follow-up being 35 months. The mechanism of injury was similar in all patients in this series, namely, a fall on the point of the shoulder.

Twenty-three of the twenty-five patients were examined and evaluated, whereas two of the patients were evaluated by telephone.

Of the patients evaluated, more than one-half were noted to have no pain of any type. The remainder, with one exception, have had occasional discomfort without compromise in activity. One patient who had mild discomfort was a weightlifter who had pain only when actually lifting weights, but otherwise suffered no limitations of activity. Function was normal in all patients and no deformity was noted. There was a reduction in internal rotation in three of the patients, the internal rotation being reduced to seventy degrees as opposed to the normal internal rotation of ninety degrees. As can be seen from the above sample of results obtained with prosthesis in accordance with the present invention, the prosthesis last for at least six years, cause only minimal discomfort, yield the subjects a good range of motion, and produce no deformity following surgery. Many patients return to relatively normal activities within two weeks. This return to early activity has decreased the morbidity associated with this type of injury.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be used to fall therebetween.

What is claimed is:

1. A method of preparing a prosthesis for repair, supplement or replacement of a damaged ligament or tendon, comprising the step of treating an elongated strip of polyethylene terephthalate, henceforth termed "Dacron" and having two surfaces, with a shrinking agent under conditions such that only lengthwise shrinkage is prevented, said treatment being continued for a period long enough to effect a substantial reduction in the lengthwise extensibility of said strip.

2. The method as defined in claim 1, further comprising the steps of bringing said strip into tubular form subsequent to treating with said shrinking agent, placing said strip in tubular form on a mandrel and heat-treating said strip for a sufficiently long period at a sufficiently elevated temperature to heat-set said strip into tubular form.

3. The method as defined in claim 2, wherein said strip is initially a single layer with two long edges and is brought into tubular form by joining said long edges together.

4. The method as defined in claim 2, wherein said strip is initially a circularly-knit, flattened tube.

5. The method as defined in claim 2, wherein said strip is initially a warp-knit, flattened tube.

6. The method as defined in claim 2, wherein said strip in tubular form has at least one lengthwise ridge extending from a surface thereof.

7. The method as defined in claim 1, wherein at least one surface of said strip is a velour.

8. The method as defined in claim 1, wherein both surfaces of said strip are velours.

9. The method as defined in claim 1, wherein said shrinking agent is $CH_2Cl_2$.

10. The method as defined in claim 1, wherein said shrinking agent is a combination of $CH_2Cl_2$ and $NO_2$.

11. The method as defined in claim 1, wherein said treatment with shrinking agent is carried out under conditions such as to reduce the extensibility of said strip by at least about 50%.

12. A method of treating a patient suffering from a damaged ligament or tendon, comprising the step of substituting for at least a part of said ligament or tendon a polyethylene terephthalate fabric strip of extensibility reduced in the longitudinal direction by at least about 50% by treatment with a shrinking agent under tension, the term "fabric" being taken to include woven, circularly-knit and warp-knit goods.

13. A prosthesis suitable for repair of a damaged ligament or tendon, comprising a polyethylene terephthalate fabric strip of reduced extensibility in the longitudinal direction, the term "fabric" being taken to include woven, circularly-knit and warp-knit goods, the extensibility of said ligament or tendon being characteristic of a strip which has been treated with a shrinking agent under conditions such as to reduce the extensibility thereof by at least about 50%.

14. The prosthesis as defined in claim 13, wherein said fabric has at least one velour surface.

15. The prosthesis as defined in claim 13, wherein said strip has an open lumen in the longitudinal direction thereof.

16. The prosthesis as defined in claim 13, wherein said strip has a tubular portion and includes at least one longitudinally-extending ridge on the surface of said tubular portion, each of said ridges having opposing faces joined to each other.

17. The prosthesis as defined in claim 13, wherein said strip is in tubular form with an open lumen and has a rigidity characteristic of a strip which has been treated with a shrinking agent under conditions such as to reduce the shrinkage thereof by at least about 50%, and heat-set on a mandrel.

* * * * *